United States Patent [19]
Poncet

[11] Patent Number: 5,833,694
[45] Date of Patent: Nov. 10, 1998

[54] STENT ASSEMBLY AND METHOD OF USE

[75] Inventor: Philippe Poncet, Fremont, Calif.

[73] Assignee: Medtronic, Inc., Minneapolis, Minn.

[21] Appl. No.: 857,983

[22] Filed: May 16, 1997

Related U.S. Application Data

[63] Continuation of Ser. No. 450,200, May 25, 1995, abandoned.

[51] Int. Cl.⁶ .................................................. A61B 17/00
[52] U.S. Cl. .......................................................... 606/108
[58] Field of Search ................................... 606/108, 198, 606/191, 141; 604/62

[56] References Cited

U.S. PATENT DOCUMENTS

| | | | |
|---|---|---|---|
| 3,334,679 | 8/1967 | Cohn ........................................ | 606/194 |
| 3,989,049 | 11/1976 | Yoon ..................................... | 606/141 X |
| 4,154,239 | 5/1979 | Turley ................................... | 604/62 X |
| 4,226,239 | 10/1980 | Polk et al. ............................. | 606/141 |
| 4,493,319 | 1/1985 | Polk et al. ............................. | 606/141 |
| 4,576,591 | 3/1986 | Kaye et al. ............................ | 604/62 |
| 4,580,568 | 4/1986 | Giantureo .............................. | 128/345 |
| 4,665,906 | 5/1987 | Jervis .................................... | 128/92 YN |
| 4,687,465 | 8/1987 | Prindle et al. ......................... | 604/62 X |
| 4,727,873 | 3/1988 | Mobin-Uddin ........................ | 606/200 |
| 4,873,978 | 10/1989 | Ginsburg ............................... | 606/200 X |
| 4,976,686 | 12/1990 | Ball et al. .............................. | 604/62 X |
| 5,026,377 | 6/1991 | Burton et al. ......................... | 606/108 |
| 5,035,706 | 7/1991 | Giantureo et al. .................... | 606/198 |
| 5,192,297 | 3/1993 | Hull ....................................... | 606/195 |
| 5,192,310 | 3/1993 | Herweck ............................... | 623/1 |
| 5,197,978 | 3/1993 | Hess ...................................... | 623/1 |
| 5,201,757 | 4/1993 | Heyn et al. ............................ | 606/198 |
| 5,219,355 | 6/1993 | Parodi et al. .......................... | 606/191 |
| 5,226,889 | 7/1993 | Sheilban ................................ | 604/101 |
| 5,290,310 | 3/1994 | Markower et al. ................... | 606/108 X |
| 5,292,331 | 3/1994 | Boneau ................................. | 606/198 |
| 5,306,294 | 4/1994 | Winston et al. ....................... | 623/1 |
| 5,312,415 | 5/1994 | Palermo ................................ | 606/108 |
| 5,334,209 | 8/1994 | Yoon ..................................... | 606/141 |

FOREIGN PATENT DOCUMENTS

| | | | |
|---|---|---|---|
| 228022 | 8/1959 | Australia .............................. | 604/62 |
| 2132898 | 7/1984 | United Kingdom ................. | 606/108 |

OTHER PUBLICATIONS

"Gianturco–Rosch Biliary Z–stents" 1989.
Schneider "Wallstent" 1994.

*Primary Examiner*—Michael H. Thaler
*Attorney, Agent, or Firm*—Sheldon & Mak

[57] ABSTRACT

The invention is a method for deploying a stent including the steps of providing a sheath containing a plurality of stents; locating the distal end of the sheath at a treatment site in a passage; and moving the sheath and a first stent relative to each other a distance sufficient to expose the first stent to the passage by actuating a stent deployment mechanism disposed at the proximal end of the sheath, the distance being determined solely by the structure of the stent deployment mechanism. The invention also includes a stent assembly comprising a sheath; a stent stop within the sheath at the distal end of the sheath; a stent disposed against the stent stop; an actuator; and an actuator limit stop. Also included within the invention is a stent loading mechanism.

16 Claims, 8 Drawing Sheets

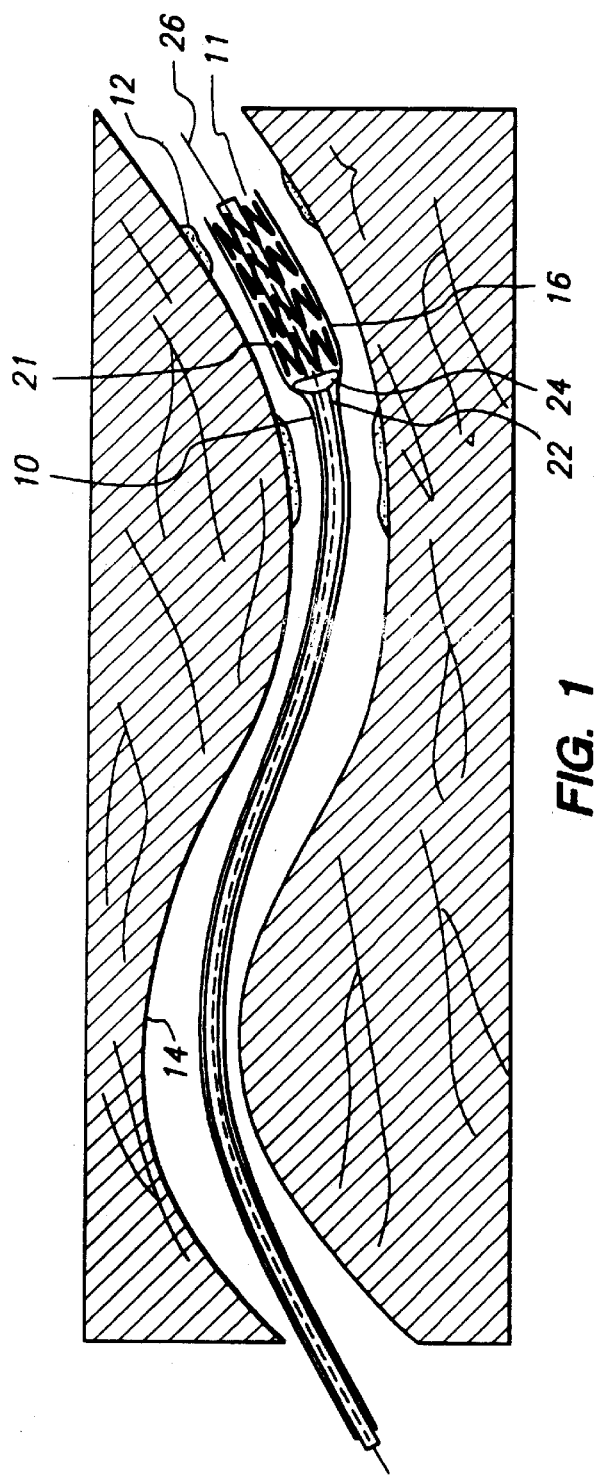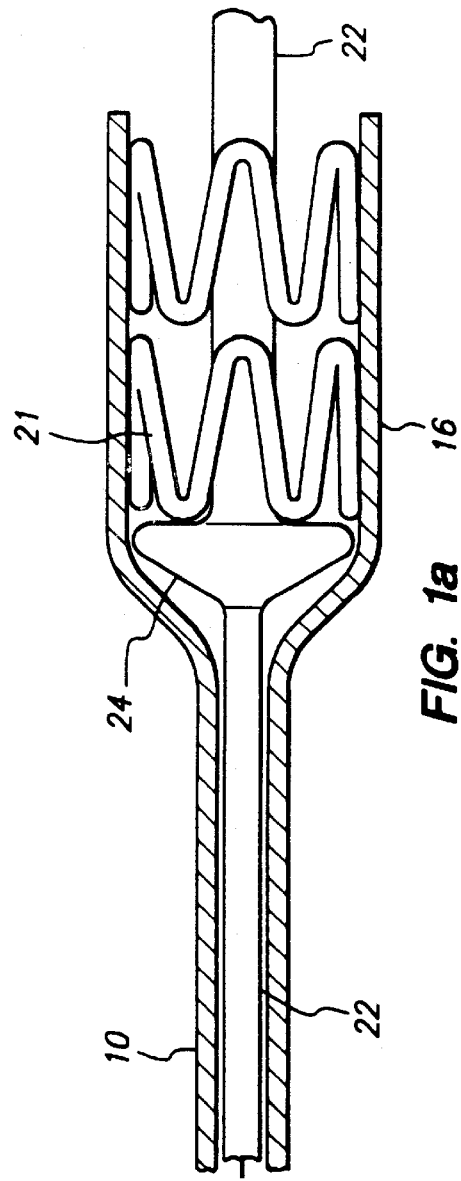

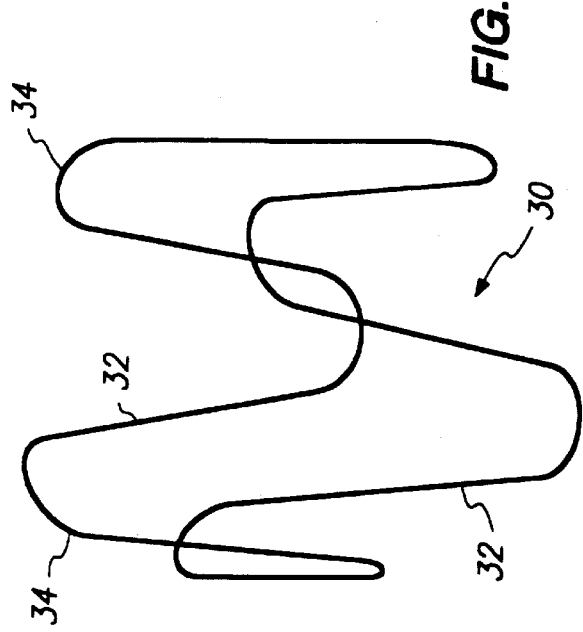
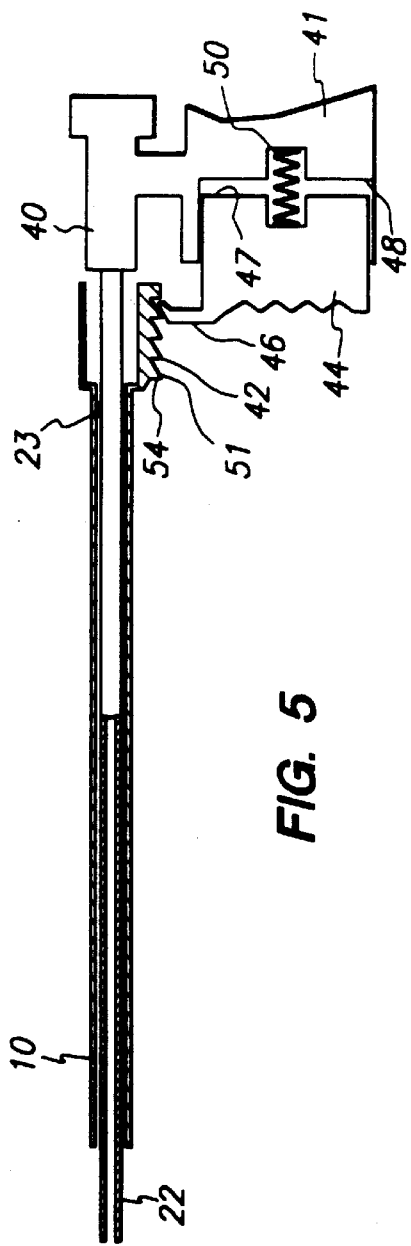

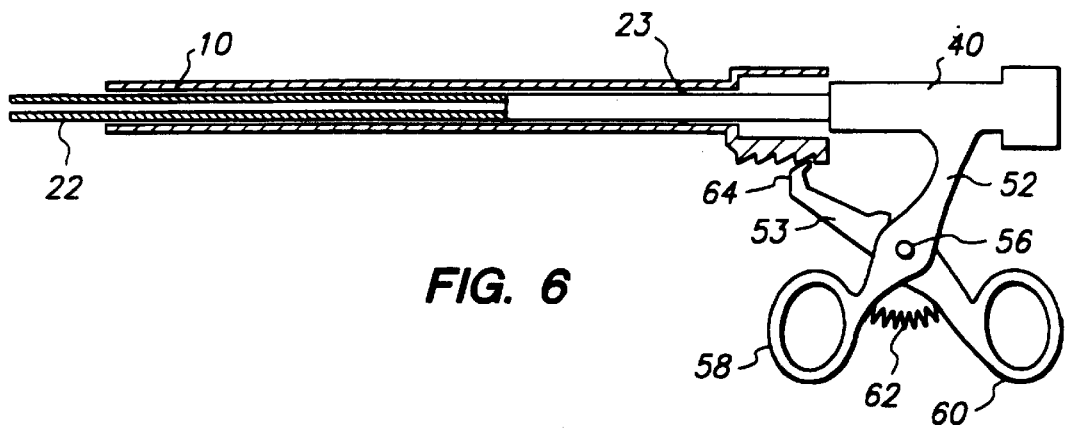
FIG. 6
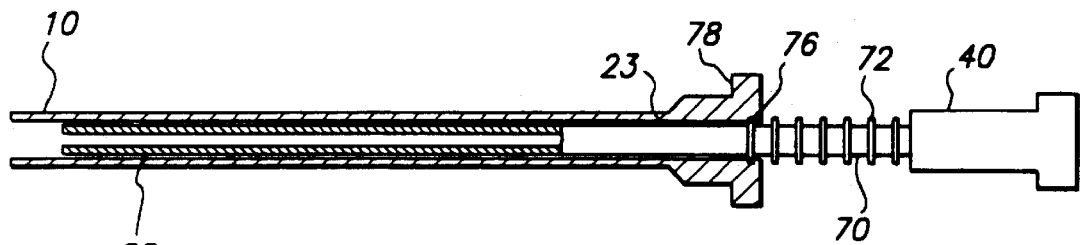
FIG. 7
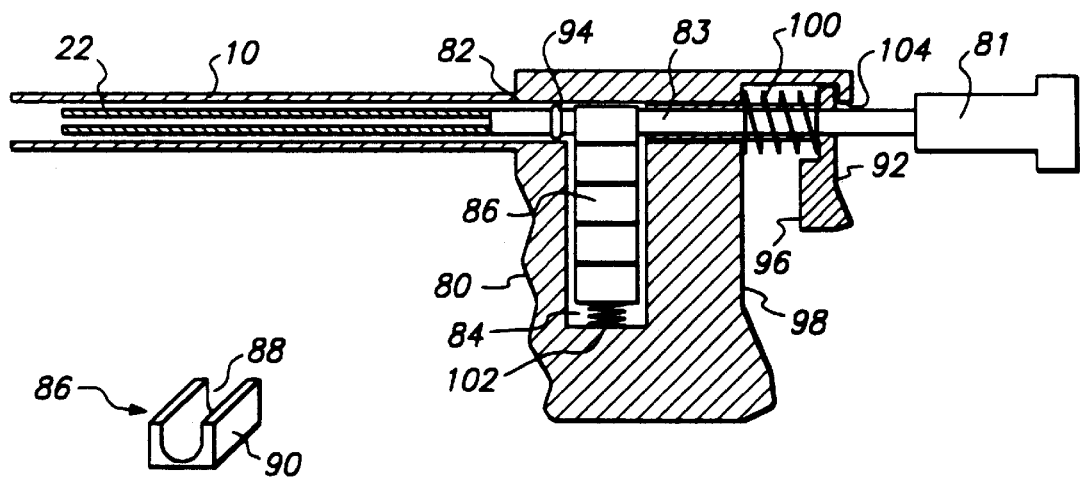
FIG. 8
FIG. 9

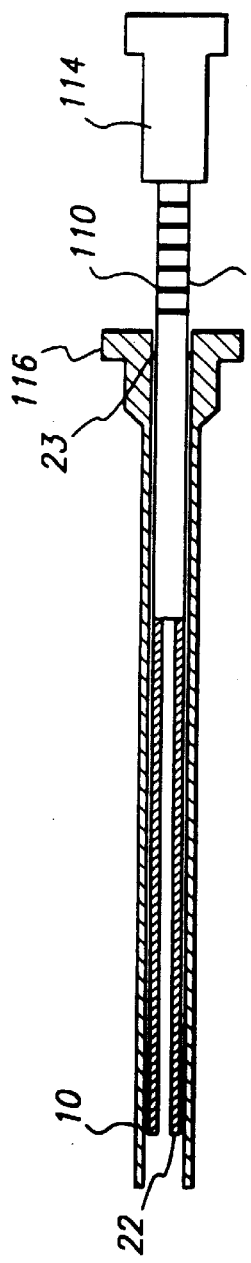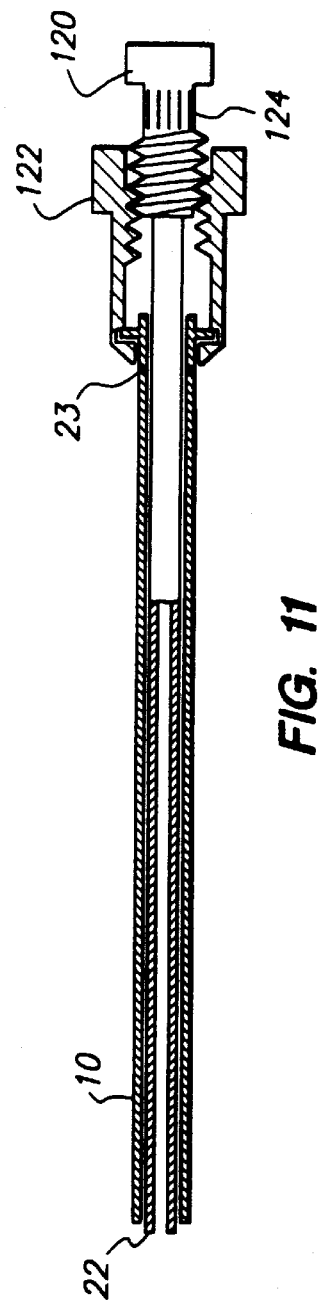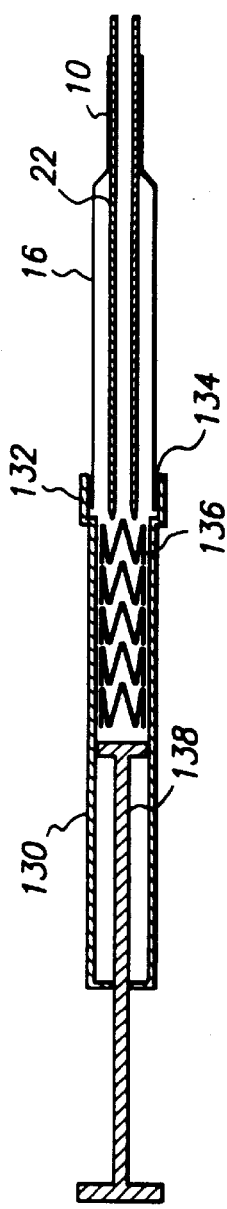

STENT ASSEMBLY AND METHOD OF USE

This is a continuation of application Ser. No. 08/450,200 filed May 25, 1995 now abandoned.

BACKGROUND OF THE INVENTION

1. Field of the Invention

This invention relates to generally to the placement of stents in body passages. In particular, the invention relates to a method for inserting stents at multiple sites within body passages and a stent assembly for practicing that method.

2. Brief Description of the Prior Art

Stents are mechanical endoprosthetic devices for use in expanding and/or supporting passages within a patient's body, such as blood vessels, bronchial tubes and biliary ducts. Stents are typically delivered to a treatment site in a compressed form via a catheter. After placement, the stents expand, or are expanded, to press against the passage walls.

Stents come in a variety of designs. For example, Gianturco U.S. Pat. No. 4,580,568 describes an endovascular stent formed from stainless steel wire bent into a zig-zag pattern. In its compressed form, the Gianturco '568 stent is placed inside a sheath and pushed to the sheath's distal end by a flat-ended pusher. With the sheath's distal end at the treatment site, the pusher is held in place while the sheath is withdrawn to expose the stent within the blood vessel. The stent then self-expands to contact the blood vessel wall. One drawback of the Gianturco '568 system, however, is that only one stent at a time may be loaded into the sheath. The pusher must be withdrawn and a single stent inserted and pushed to the sheath's distal end each time a stent is placed within a blood vessel.

Gianturco U.S. Pat. No. 5,035,706 describes a similar arrangement. Here, however, two or more stents are attached to each other to form, in effect, a single larger stent for use in situations in which a smaller stent is not large enough. The relative positions of the interlocked stents are fixed prior to deployment, however. In addition, the Gianturco '706 system does not permit the placement of multiple stents at multiple, separate treatment sites within the blood vessel or other body passage.

Winston U.S. Pat. No. 5,306,294 describes a self-expanding stent formed as a coiled sheet. One or more of the coiled sheets are disposed on a spool within a sheath. The proximal end of each coiled sheet abuts a flange on the spool. When the distal end of the sheath is at a treatment site, the spool is advanced, and the flange pushes the stent outside the sheath, thereby permitting the stent to expand. Winston does not describe the means by which the relative movement between the sheath and the spool is accomplished, however. Winston therefore does not address the question of how accidental deployment of more than one stent at a given treatment site may be avoided.

Boneau U.S. Pat. No. 5,292,331 describes a stent that is not self-expanding but must instead be expanded by a balloon once the stent is in place. The Boneau device permits placement of multiple stents along the balloon catheter for simultaneous deployment at multiple sites within the body passage. The relative positions of the stents are set prior to insertion of the balloon catheter into the body, however. In addition, all stents must be deployed simultaneously, leaving no possibility for the attending physician to decide the number and relative placement of stents while the procedure is being performed.

Other stent designs are described by Heyn U.S. Pat. No. 5,201,757; Parodi U.S. Pat. No. 5,219,355; Hull U.S. Pat. No. 5,192,297; Sheiban U.S. Pat. No. 5,226,889; and Hess U.S. Pat. No. 5,197,978. The disclosures of each of the above references are incorporated herein by reference.

SUMMARY OF THE INVENTION

One object of this invention is to provide a stent and stent deployment device that permit safe and accurate placement of multiple stents at multiple treatment sites within a body passage without completely withdrawing any part of the deployment device from the patient's body.

Another object of this invention is to provide a stent loading method and apparatus that enable the user to load the number of stents desired to perform the stent procedure.

In a preferred embodiment, the invention is a method for deploying a stent, including the steps of providing a sheath containing a plurality of compressed self-expanding stents, each stent comprising a bent wire formed in a closed configuration; locating the distal end of the sheath at a treatment site in a passage; moving the sheath and a first stent relative to each other a distance sufficient to expose the first stent to the passage, thereby permitting the first stent to expand; and moving the distal end of the sheath without exposing a second stent.

Another preferred embodiment of the invention is a method for deploying a stent including the steps of providing a sheath containing a plurality of stents; locating the distal end of the sheath at a treatment site in a passage; and moving the sheath and a first stent relative to each other a distance sufficient to expose the first stent to the passage by actuating a stent deployment mechanism disposed at the proximal end of the sheath, the distance being determined solely by the structure of the stent deployment mechanism.

In another embodiment, the invention is a stent assembly comprising a sheath; a stent stop within the sheath at the distal end of the sheath; a stent disposed against the stent stop; an actuator; and an actuator limit stop.

In yet another embodiment, the stent assembly of this invention comprises a sheath; a tube disposed within the sheath; a stent stop within the sheath at the distal end of the sheath; a stent disposed around the tube and against the stent stop; and an actuator comprising a hub attached to the tube, the hub having markings indicating the amount of relative movement between the tube and the sheath necessary to move the stent outside the sheath.

The invention also includes a stent loading mechanism comprising a cartridge having an open end, and a plunger movably disposed within the cartridge, the cartridge containing a plurality of stents disposed between the plunger and the open end. In an alternative embodiment, the stent loading mechanism of this invention may comprise a sheath holder, a pusher and a stent cartridge holder between the sheath holder and the pusher.

The invention is described in more detail below with reference to the drawings.

BRIEF DESCRIPTION OF THE DRAWINGS

FIG. 1 is a schematic drawing of a part of a stent assembly showing placement of a sheath and a first stent at a first treatment location within a passage.

FIG. 1a is a cross-sectional view of the distal end of a stent assembly.

FIG. 4 is a perspective view of a stent formed according to a preferred embodiment of this invention.

FIG. 5 is a cross-sectional drawing of a stent deployment mechanism according to one embodiment of this invention.

FIG. 6 is a cross-sectional drawing of a modification to the stent deployment mechanism of FIG. 5.

FIG. 7 is a cross-sectional drawing of a stent deployment mechanism according to another embodiment of the invention.

FIG. 8 is a cross-sectional drawing of a stent deployment mechanism according to yet another embodiment of the invention.

FIG. 9 is a perspective drawing of a spacer used in the stent deployment mechanism of FIG. 8.

FIG. 10 is a cross-sectional drawing of a stent deployment mechanism according to another embodiment of the invention.

FIG. 11 is a cross-sectional drawing of a stent deployment mechanism according to yet another embodiment of the invention.

FIG. 12 is cross-sectional drawing of a stent loading mechanism according to one embodiment of the invention.

DETAILED DESCRIPTION OF THE PREFERRED EMBODIMENTS

The stent deployment method of this invention permits serial deployment of multiple stents in a patient at multiple treatment sites within a passage (such as a blood vessel, bile duct, urinary tract, esophagus, tracheobronchial tree, etc.) without removing the delivery tool from the passage to reload the tool. A preferred embodiment of the method uses self-expanding stents. Before the start of the procedure, multiple stents are compressed and placed in the distal end of a catheter sheath. The sheath is then inserted into the passage until the distal end of the sheath is located at a first treatment site in the passage. The sheath and a first stent are then moved relative to each other a distance sufficient to expose the first stent to the passage by actuating a stent deployment mechanism disposed at the proximal end of the sheath. The distance of the relative movement between the sheath and the first stent is determined solely by the structure of the stent deployment mechanism, thereby permitting the stent to expand radially within the passage.

The most common way to determine whether the distal end of the sheath is at the desired treatment site is through the use of some imaging technique, such as fluoroscopy. During deployment of the stent, the sheath is preferably moved back while the stent remains stationary. This arrangement helps ensure that the stent is deployed accurately at the treatment site. Alternatively, however, the stent can be moved forward while the sheath remains stationary.

After deployment of the first stent, the sheath and any remaining stents are moved together away from the first treatment site. A second stent may be deployed at a second treatment site within a passage without completely removing the sheath from the passage by moving the sheath's distal end to the second treatment site and then moving the sheath and a second stent relative to each other by a distance sufficient to expose the second stent to the passage. Once again, deployment is achieved by actuating a stent deployment mechanism disposed at the proximal end of the sheath, with the distance being determined solely by the structure of the stent deployment mechanism. After deployment, the second stent expands radially within the passage at the second treatment site.

While this invention can be used with a variety of stent designs, the method works best if each stent has a relatively short length. Using multiple short stents instead of a few long stents keeps the catheter's distal end more flexible for better maneuverability (better trackability) through tortuous vessels, thereby limiting injury to the vessels. Short stents are also useful for scaffolding lesions in very tight vessel curves. Finally, the use of multiple short stents enables the attending physician to limit the total amount of metal (or other stent material) to limit thrombogenicity.

Figure 2:
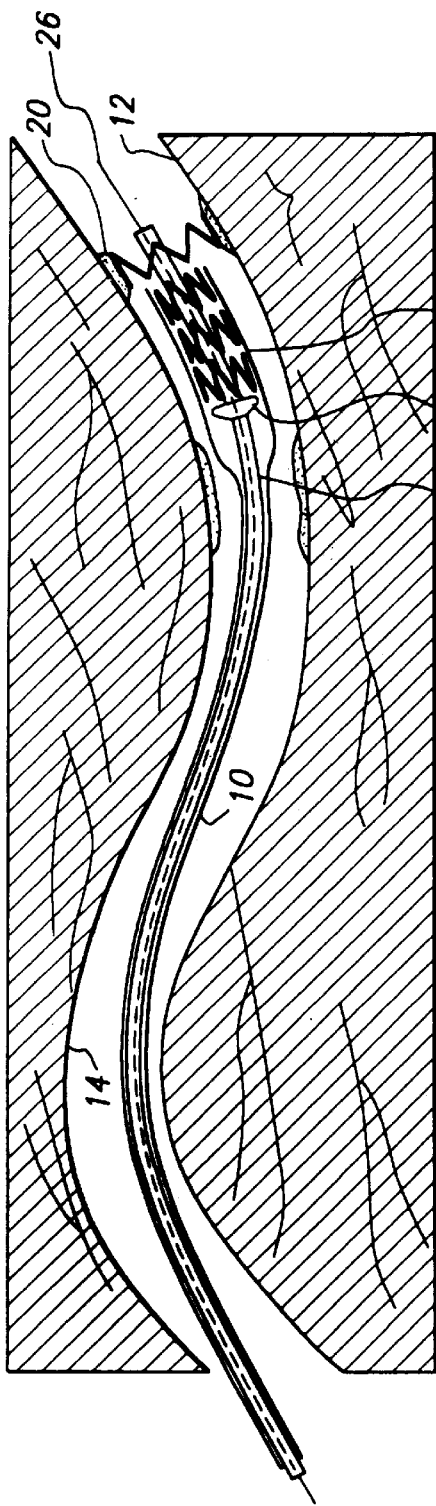
FIG. 2 is a schematic drawing of the stent assembly of FIG. 1 showing deployment of the first stent at the first treatment location.
Figure 3:
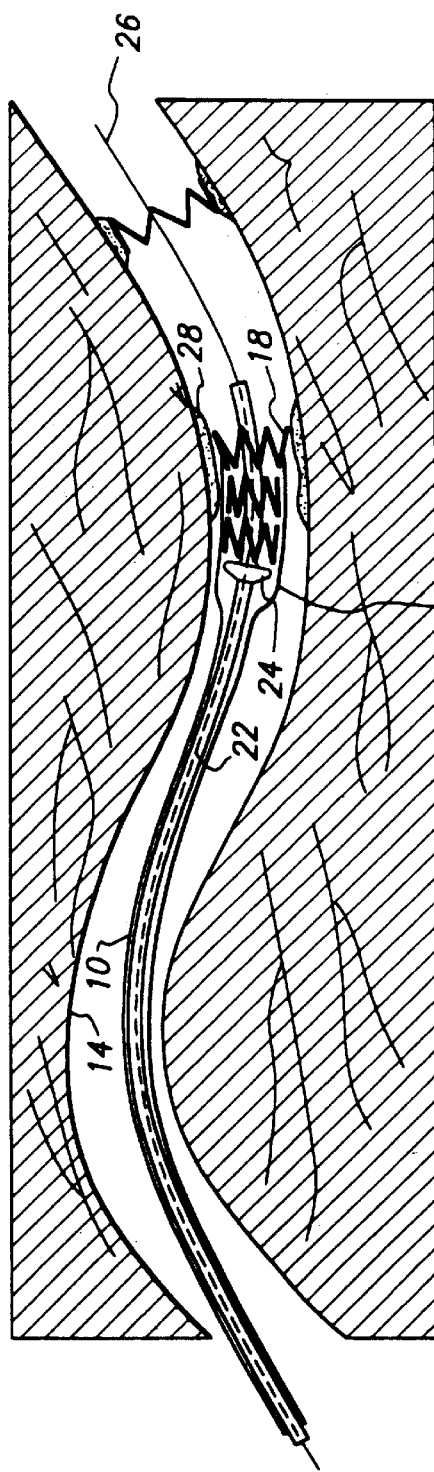
FIG. 3 is a schematic drawing of the stent assembly of FIGS. 1 and 2 showing placement of the sheath and a second stent at a second treatment.

An example of a stent assembly employing this procedure is shown in FIGS. 1–3. FIG. 1 shows the distal end 11 of a sheath 10 located at a treatment site 12 within a blood vessel 14. Sheath 10 has an enlarged portion 16 at its distal end. A plurality of self-expanding stents are disposed in a compressed state within the enlarged portion of sheath 10. In this example, each stent is formed as a bent wire, as shown in more detail in FIG. 4. Other self-expanding stent designs, such as slotted tubes, may be used with this invention, however.

In this example, the stents are disposed around a tube 22 within the lumen of sheath 10. Tube 22 has a shoulder 24 forming a stent stop against which the innermost stent 21 rests. Tube 22 surrounds a guidewire 26 used to guide the stent assembly through the patient's blood vessels to the treatment site in a manner known in the art. Shoulder 24 can be seen more clearly in FIG. 1a, which is a cross-section of a smaller stent assembly designed to hold two stents.

After confirmation that the sheath's distal end is at the desired treatment site, the outermost stent 20 is deployed by maintaining tube 22 stationary while moving sheath 10 back a distance corresponding to the length of stent 20, thereby permitting stent 20 to expand as shown in FIG. 2. This relative movement between sheath 10 and tube 22 is accomplished by actuating a stent deployment mechanism, such as one of the mechanisms shown in FIGS. 5–9 below. In any event, the distance of the relative movement of the sheath and tube is preferably dictated solely by the structure of the stent deployment mechanism.

After deployment of the first stent, the sheath's distal end may be moved to a second treatment site 28, as shown in FIG. 3. The stent deployment procedure is then repeated to deploy a second stent 18 at the second treatment site.

In the previous example, the stent assembly had a fall complement of stents. In other words, the innermost stent 21 was abutting shoulder 24, and the outermost stent 20 was at the distal end of sheath 10. If, however, fewer stents had been loaded into sheath 10 prior to the commencement of the procedure, the user would have to actuate the stent deployment mechanism once for each missing stent to bring shoulder 24 up against the innermost stent before there is any relative movement between the sheath and the outermost stent to expose the stent.

FIG. 4 shows a preferred stent design for use with the stent assembly and stent deployment method of this invention. Stent 30 is preferably made from superelastic NiTi (or one of its alloys) wire formed in a zig-zag configuration, for example, as described in Jervis U.S. Pat. No. 4,665,906, which is hereby incorporated by reference for all purposes. This configuration includes a series of straight sections 32 joined by bends 34 at the ends of the straight sections. In the expanded state shown in FIG. 4, the stent forms a substantially cylindrical open wall. In its compressed form, the stent fits within the sheath of a stent deployment mechanism, as described above. The size of the stent depends on its intended application. For example, for coronary applications, the stent length should be approximately 4–6 mm.

One advantage of NiTi alloys is their high recovery ratio at self-expansion, which permits a greater degree of stent compression within the delivery catheter. Smaller catheters track better and can more easily traverse tight lesions and/or stents already in place. In addition, the low Young's modulus of NiTi makes it a less traumatic material than stainless steel.

Other stent designs may be used with the method and apparatus of this invention. Preferably, the length of the stents should change no more than 20% between their compressed and expanded states. In addition, in an effort to limit thrombogenicity and promote epithelialization, the actual surface area of the stent in its expanded state should be less than 10–20% of the surface area of a cylinder having the same length.

The stents should be designed so that their free recovered shape is always slightly larger than the maximum vessel diameter for which they are prescribed. This feature minimizes the possibility of stent recoil pulling the stent away from the vessel wall and minimizes the risk of stent migration. Also, in its superelastic state (i.e., plateau stress on a stress-strain curve), the stent will exert a fairly constant pressure and act more like a "live" structure inside the vessel. In other words, the stent will exert a constant pressure as the vessel expands and contracts, such as during spasms.

The stents should also be radiopaque in order to be visible during fluoroscopy. Optionally, the stents may be coated with material to minimize thrombogenicity, minimize flow perturbance, to allow local drug delivery, etc. The stents may also be provided with one or more barbs to prevent migration. Other stent materials include stainless steel, titanium, tantalum, palladium, cobalt-chromium alloys and biodegradable plastics.

A variety of stent deployment mechanisms may be used with this invention. Each of the embodiments shown in FIGS. 5–9 has an actuator (i.e, a mechanism that moves the sheath and stent with respect to each other) and an actuator limit stop (i.e., a mechanism that limits the motion of the actuator). The interaction between the actuator and the actuator limit stop determines the amount of relative motion between the sheath and a stent loaded in the sheath's distal end.

If the stent deployment mechanism will be used to deploy multiple stents without removing the sheath from the passage for reloading, the stent deployment mechanism also preferably has some way to provide for multiple identical actuations. Each of the embodiments shown in FIGS. 5–9 also has a lever for increasing the actuating force.

It should be noted that FIGS. 5–9 are provided for exemplary purposes only and are only some of the many ways this invention can be implemented.

FIG. 5 shows an embodiment of a stent deployment mechanism in which the actuator includes a hub 40 attached to tube 22, a handle 41 extending from the hub, a series of teeth 42 extending radially outward from sheath 10, and a tooth engagement member 44. A seal or hemostatic valve 23 is provided between the tube and the sheath. The tooth engagement member is movable along the sheath's longitudinal axis and has a finger 46 extending toward, and mating with, teeth 42. Movement of member 44 is limited, however, by the interaction of its surface 47 with a facing surface 48 on handle 41, which together form the actuator limit stop of this embodiment. The length of this movement corresponds to the distance the sheath must move relative to the tube (and, therefore, relative to a stent disposed in the sheath's distal end) in order to expose a stent for deployment. In other words, the distance is the length of a compressed stent measured along the sheath's longitudinal axis, plus an inter-stent distance within the sheath.

In use, the operator squeezes member 44 toward handle 41 until surfaces 47 and 48 abut. This action will deploy a stent disposed in the sheath's distal end. When member 44 is released, a spring 50 moves member 44 distally. The cam face 51 on the back of teeth 42 permits the finger 46 of member 44 to move from one tooth to the next tooth, until it falls into place against the radial face 54 of the next tooth. The stent deployment mechanism is then ready to deploy the next stent. During deployment, each tooth serves as a lever to help move the sheath and stent with respect to each other.

FIG. 6 shows a modification to the embodiment of FIG. 5. In this embodiment, the handle 52 and tooth engagement member 53 are connected by a pivot 56. As before, facing surfaces 58 and 60 serve as an actuator limit stop to limit the relative movement of the handle and tooth engagement member (and, therefore, the relative movement of the sheath and tube), and a spring 62 moves the finger 64 of the tooth engagement member up to the next tooth.

Yet another embodiment is shown in FIG. 7. Disposed between tube 22 and hub 40 is a hub extension 70. (This element can also be thought of as part of tube 22.) A series of circumferential projections or ridges 72 are formed on the hub extension. The interaction of ridges 72 and a corresponding indentation or groove 76 formed in the sheath 10 constitute the actuator limit stop of this embodiment. A flange 78 provides a lever for the operator to use when moving the hub (and hence the tube and stent) with respect to the sheath. To use the stent deployment mechanism of this embodiment, the operator simply pushes the hub forward toward the distal end of the sheath while holding the flange 78 or other part of the sheath. The resilient nature of the sheath causes it to deform to allow the ridge to leave the groove. The hub may be moved forward until the next ridge lines up with the groove, at which time the resilient action of the sheath latches onto the ridge to hold the hub in place. The spacing between ridges corresponds to the distance the sheath must move relative to the tube (and, therefore, relative to a stent disposed in the sheath's distal end) in order to expose the stent for deployment.

FIGS. 8 and 9 show yet another approach. This embodiment has a handle 80 extending from sheath 10 distally from the hub 82. Handle 80 may be integral with sheath 10 as shown in FIG. 8 or it may be a separate element attached to the sheath. In any event, a lumen 82 corresponding to the lumen of sheath 10 is formed in handle 80. A hub extension 83 (or, alternatively, an extension of tube 22) runs between tube 22 and hub 81 in lumen 82.

Also formed in handle 80 is a chamber 84. Disposed in chamber 84 are a plurality of spacers 86, with the topmost spacer surrounding hub extension 83 in lumen 82. As shown in FIG. 9, the spacers 86 are formed with an open side 88 to permit the spacer to surround the hub extension and with flat sides 90 to maintain the spacers'orientation in the chamber with the open sides up.

In this embodiment, the actuator includes a plunger 92 acting together with the topmost spacer and a shoulder 94 on the hub extension. The actuator limit stop includes one surface 96 of the plunger and a facing surface 98 on the handle. The handle provides a lever to add force to the operation of the deployment mechanism.

In use, the operator moves the plunger 92 forward, i.e., toward the distal end of the sheath. The front face of the plunger moves the topmost spacer forward with respect to the sheath, which moves the shoulder 94 and tube 22 forward with respect to the sheath, which exposes a stent disposed in the sheath's distal end. Forward movement of the plunger is limited by the interaction of the face 96 of the plunger and the face 98 of the handle. The distance from the plunger's starting position (shown in FIG. 8) and its limit position corresponds to the distance the sheath must move relative to the tube (and, therefore, relative to a stent disposed in the sheath's distal end) in order to expose the stent for deployment.

This distance also corresponds to the length of each spacer 86. Thus, when a spring 100 moves plunger 92 back to its initial position, a spring 102 disposed at the bottom of chamber 84 pushes a new spacer up into lumen 82 to surround hub extension 83. In this position, the new spacer lies adjacent the first spacer, so that when the plunger is moved forward to deploy the next stent, the plunger moves both spacers (and, therefore, tube 22) forward with respect to sheath 10. A stop 104 extending down behind plunger 92 limits backward motion of the plunger under the operation of spring 100.

FIGS. 10 and 11 show embodiments in which the stent deployment mechanism provides visual indications to limit relative movement of the sheath and stent. The embodiment shown In FIG. 10 has visual markings 110 formed on an extension 112 of hub 114. The space between markings corresponds to the distance the sheath 10 must move relative to the tube 22 (and, therefore, relative to a stent disposed in the sheath's distal end) in order to expose the stent for deployment. To deploy a stent, the hub is moved forward until the marking closest to the flange 116 lines up with the edge of flange 116.

FIG. 11 is a variation of the embodiment of FIG. 10. In this embodiment, the hub 120 is threaded, as is a knob 122 extending from the proximal end of sheath 10. The distance between longitudinal markings 124 on hub 120 correspond to the distance the sheath 10 must move relative to the tube 22 (and, therefore, relative to a stent disposed in the sheath's distal end) in order to expose the stent for deployment. In its initial position, one of the markings lines up with a marking on the front face (not shown) of knob 122. To deploy a stent, hub 120 is rotated into knob 122 until the next mark lines up with the marking on the knob's front face.

The number of stents needed to perform a given procedure will vary from procedure to procedure. The invention therefore also provides a stent loading mechanism for loading only the number of stents necessary to perform the desired medical procedure.

Figure 13:
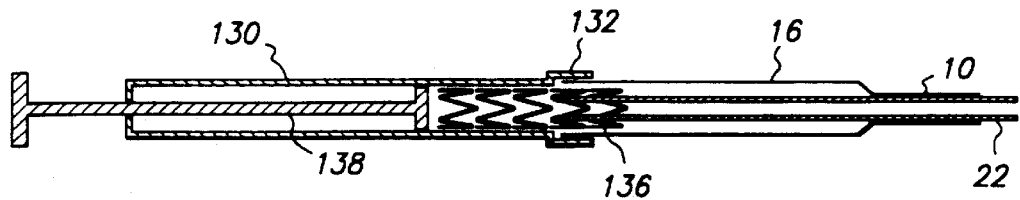
FIG. 13 is a cross-sectional drawing of the stent loading mechanism of FIG. 12 being used to load two stents into a sheath.
Figure 14:
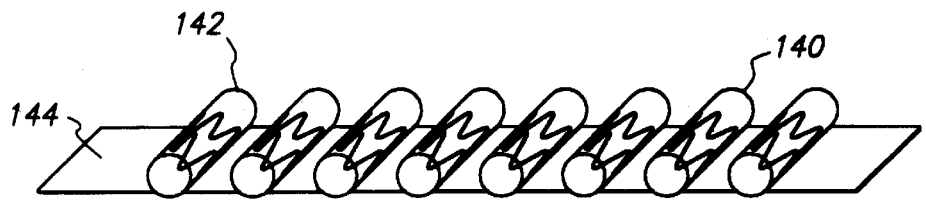
FIG. 14 is a perspective drawing of stents, stent cartridges and a carrier for use with another embodiment of a stent loading mechanism.

FIGS. 12 and 13 show one embodiment of a stent loading mechanism according to this invention. A stent cartridge 130 has an enlarged portion 132 at an open end 134 which is designed to mate with the enlarged portion 16 of a sheath 10. The stent cartridge contains one or more compressed stents 136 which can be moved to the open end of the cartridge by a plunger 138. As shown in FIG. 13, movement of the plunger toward the open end of the cartridge pushes the stents into sheath 10 around tube 22. The user may load any number of stents into the sheath. The number of stents loaded may be seen directly if the sheath is transparent. Also, indices may be provided on the plunger to indicate how many stents have been loaded into the sheath.

Another stent loading mechanism is shown in FIGS. 14–17. Compressed stents 140 loaded individually in cartridges formed as loading tubes 142 are mounted on a carrier 144. To load stents into the distal end of a sheath, the sheath 10 is placed in a slot 146 formed in a stent loader housing 148, as shown best in FIGS. 16 and 17. The stent loading tubes 142 are placed in a stent cartridge holder, such as grooves 150 formed in a movable carrier indexer 152.

Figure 16:
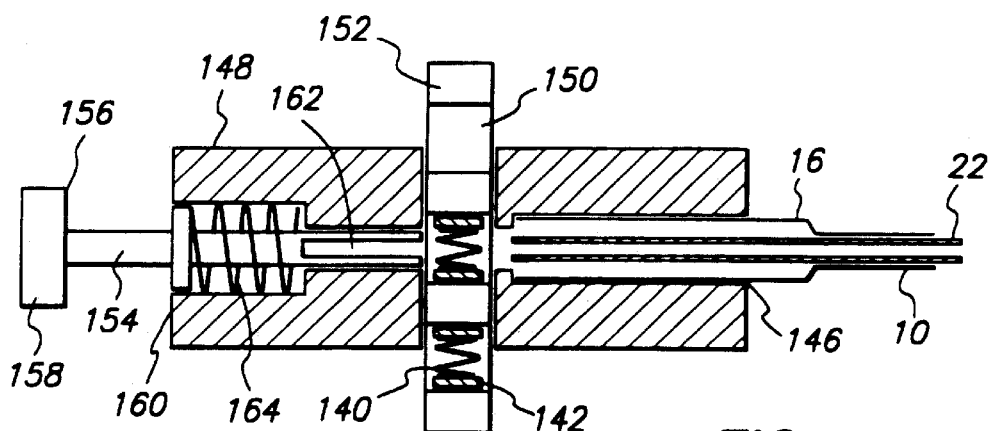
FIG. 16 is a cross-sectional drawing of the stent loading mechanism of FIG. 15
Figure 17:
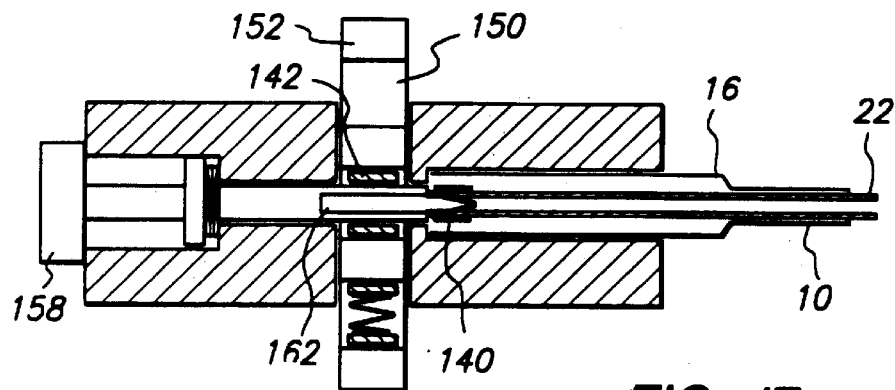
FIG. 17 is a cross-sectional drawing of the stent loading mechanism of FIGS. 15 and 16 being used to load a stent into a sheath.

To load stents into the sheath 10, the carrier indexer 152 is positioned so that a stent loading tube 142 lines up with the sheath, as shown in FIG. 16. A spring-biased pusher 154 is then moved forward until the inside face 156 of pusher head 158 meets the end face 160 of housing 148, as shown in FIG. 17. In this position, the front end 162 of pusher 154 has moved through loading tube 142 and is at the distal end of sheath 10, and the stent 140 that had been within the loading tube 142 has been pushed into the sheath, as shown. A spring 164 returns pusher 154 to its initial position, thereby enabling a new loading tube to be lined up with sheath 10 through movement of carrier indexer 152. The process can be repeated until the sheath has been loaded with the desired number of stents.

Figure 15:
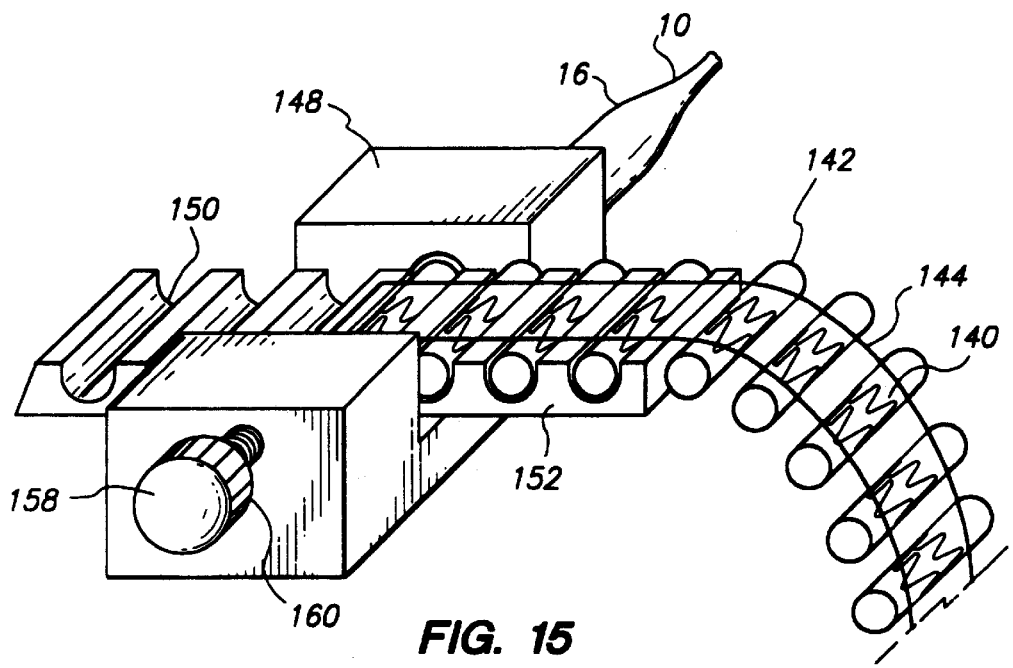
FIG. 15 is a perspective view of the stent loading mechanism for use with the stents, stent cartridges and carrier of FIG. 14.
Figure 18:
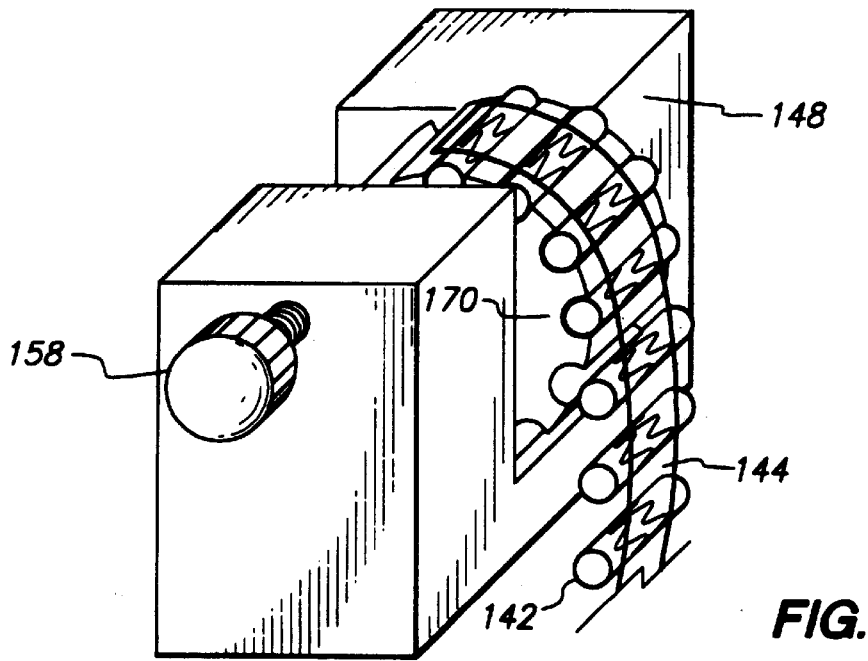
FIG. 18 is a perspective view of a stent loading mechanism according to another embodiment of the invention.

An alternative to the embodiment of FIGS. 15–17 is shown in FIG. 18. This embodiment replaces the linear carrier indexer of the previous embodiment with a circular indexer 170.

Figure 19:
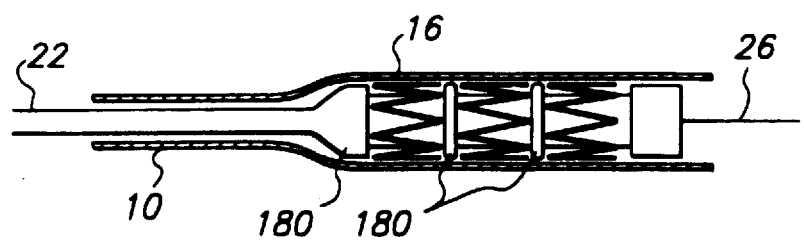
FIG. 19 is a cross-sectional view of an alternative embodiment of the stent assembly of this invention.
Figure 20:
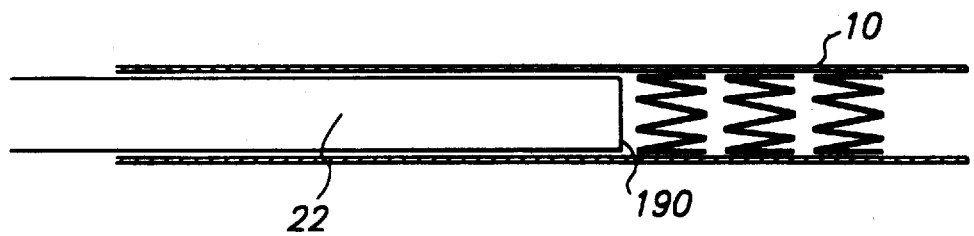
FIG. 20 is a cross-sectional view of yet another alternative embodiment of the stent assembly of this invention.

Modifications to the embodiments described above will be apparent to those skilled in the art. For example, instead of using a sheath with an enlarged distal end, the delivery catheter can be designed to have a uniform diameter. Also, instead of having adjacent stents within the sheath transmitting the pushing force to the outermost stent from a single shoulder during deployment, individual pockets or shoulders 180 may be provided for each stent in the sheath, as shown in FIG. 19. Finally, the end 190 of tube 22 can serve as a stent stop, as shown in FIG. 20.

What is claimed is:

1. A stent assembly for dispensing stents, the stent assembly comprising:
   a) an elongated sheath having a proximal end and a distal end, the distal end being sized to receive at least one stent;
   b) a stent stop movably disposed within the sheath at the distal end;
   c) an actuator disposed at the proximal end of the sheath and connected to the stent stop for moving the stent stop at the distal end, the actuator including a spacer chamber and a plurality of spacers disposed in the chambers, each spacer defining a distance of movement of the stents at the distal end for each actuation of the actuator such that the stents are dispensed individually from the distal end of the sheath; and d) an actuator limit stop disposed to limit the motion of a portion of the actuator toward the distal end, such that only one stent is dispensed from the distal end of the sheath upon each actuation of the actuator.

2. The stent assembly of claim 1, comprising a first stent disposed against the stent stop and a second stent disposed against the first stent.

3. The stent assembly of claim 1, wherein the stents are self-expanding between a compressed shape and an expanded shape, the stent having a length in the compressed shape which is at least about 80% of the stent length in the expanded shape.

4. The stent assembly of claim 1, wherein the stents are comprised of a superelastic material.

5. The stent assembly of claim 1, wherein each actuation of the actuator provides (i) simultaneous one-directional movement of the stent stop, the stents, and one spacer toward the distal end of the sheath, (ii) substantially equidistant movement of the stent stop, the stents, and one spacer within the sheath, and (iii) individual stent dispensing from the distal end of the sheath.

6. The stent assembly of claim 5, wherein each actuation of the actuator moves one spacer from the spacer chamber and toward the distal end of the sheath, such that only one stent is dispensed from the distal end.

7. The stent stop of claim 1, wherein the stent stop remains adjacent to a side of a stent that is positioned farthest from the distal end of the sheath during repeated actuation of the actuator.

8. A method for deploying stents individually in a body passage, the method comprising the steps of:

a) providing a stent assembly comprising:
  i) a sheath including a proximal portion having a proximal end and a distal portion having a distal end, the proximal portion defining a bore having a diameter and the distal end defining an enlarged chamber 1) having a diameter greater than the diameter of the bore, and 2) sized to receive a plurality of self-expanding stents each in a compressed state within the enlarged chamber;
  ii) a movable elongated member extending between the proximal portion and the distal portion within the bore; and
  iii) an actuator connected to the elongated member for moving the stents within the enlarged chamber; and
  iv) a limit stop at the proximal end of the sheath:

b) loading into the enlarged chamber of the sheath through the distal end at least a first compressed, self-expanding stent and a second compressed, self-expanding stent disposed against the first stent;

c) introducing the sheath into the body passage and locating the distal end at a treatment site; and d) moving the actuator a predetermined distance defined by the limit stop to move the sheath and the elongated member a pre-determined distance relative to each other, and to move the elongated member, the first stent and the second stent simultaneously only in a direction toward the distal end of the sheath, so as to dispense only one stent from the enlarged chamber at the treatment site, thereby causing the dispensed stent to self-expand.

9. The method of claim 8, wherein the stents are comprised of a superelastic material, and the stents are superelastically deformed when disposed in the enlarged chamber of the sheath.

10. The method of claim 8, wherein the stents have a length when compressed in the enlarged chamber of the sheath which is at least about 80% of the stent length in the expanded state.

11. The method of claim 8, wherein the stents have a length in the expanded state which is greater than the diameter of the body passage at the treatment site such that the stents exert a generally constant pressure on the body passage.

12. A method of loading stents in a stent assembly, the stent assembly including a sheath having a proximal portion and an enlarged distal end defining a chamber sized to receive a plurality of stents, the method comprising the steps of:

a) providing a loading means sized to removably couple with the enlarged distal end of the sheath;

b) providing a plurality of stents, each having a compressed shape and an expanded shape;

c) loading the stents into the loading means in the compressed shape;

d) coupling the loading means with the distal end of the sheath;

e) simultaneously moving the stents from the loading means to the chamber of the sheath such that the stents are in the compressed shape in the chamber; and f) decoupling the loading means from the distal end of the sheath.

13. The method of claim 12, wherein the stents are comprised of a superelastic material, and the stents are superelastically compressed in the compressed shape.

14. The method of claim 13, wherein the stents have a length in the compressed shape which is at least about 80% of the stent length in the expanded shape.

15. The method of claim 12, wherein the stents are adjacent to each other in the chamber.

16. The method of claim 12, wherein the stents are separated from each other by shoulders in the chamber.

* * * * *